United States Patent
Goβler et al.

(10) Patent No.: US 10,235,535 B2
(45) Date of Patent: Mar. 19, 2019

(54) TRANSMITTING MEDICAL DATA RECORDS

(71) Applicants: Thomas Goβler, Erlangen (DE); David Schottlander, Kidlington (GB); Vladyslav Ukis, Nürnberg (DE)

(72) Inventors: Thomas Goβler, Erlangen (DE); David Schottlander, Kidlington (GB); Vladyslav Ukis, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 100 days.

(21) Appl. No.: 14/945,855

(22) Filed: Nov. 19, 2015

(65) Prior Publication Data

US 2016/0148017 A1 May 26, 2016

(30) Foreign Application Priority Data

Nov. 24, 2014 (EP) .................................. 14194515

(51) Int. Cl.
*G06F 21/62* (2013.01)
*G06F 17/30* (2006.01)
*G16H 10/60* (2018.01)

(52) U.S. Cl.
CPC .... *G06F 21/6254* (2013.01); *G06F 17/30917* (2013.01); *G16H 10/60* (2018.01)

(58) Field of Classification Search
CPC .................................................. G06F 21/6254
USPC ......................................................... 726/27
See application file for complete search history.

(56) References Cited

U.S. PATENT DOCUMENTS

| 10,096,075 B2 * | 10/2018 | Dvorak ................... G06Q 50/22 |
| 2003/0015052 A1 | 1/2003 | Hulshof |
| 2008/0301805 A1 * | 12/2008 | Bharara ................ G06F 19/321 726/21 |
| 2010/0042583 A1 | 2/2010 | Gervais et al. |
| 2011/0008168 A1 | 1/2011 | Fuglsang-Petersen et al. |
| 2013/0208955 A1 * | 8/2013 | Zhao ....................... G06F 19/321 382/128 |

FOREIGN PATENT DOCUMENTS

| DE | 19857914 A1 | 7/2000 |
| DE | 10134245 A1 | 2/2003 |
| DE | 102009032667 A1 | 1/2011 |

(Continued)

OTHER PUBLICATIONS

Hmood et al. "Privacy-Preserving Medical Reports Publishing for Cluster Analysis" 2014 IEEE; 978-1-4799-3223-8/14/$31.00 © 2014 IEEE (Year: 2014).*

(Continued)

*Primary Examiner* — Khalil Naghdali
(74) *Attorney, Agent, or Firm* — Lempia Summerfield Katz LLC

(57) ABSTRACT

The present embodiments relate to a method for transmitting medical data records. The method includes receiving a patient data record from an internal data storage unit, selecting an anonymization setting from a set of predetermined anonymization settings, generating an anonymized patient data record on the basis of the selected anonymization setting or rule, and transmitting the anonymized patient data record to an external data storage unit.

20 Claims, 10 Drawing Sheets

(56) References Cited

FOREIGN PATENT DOCUMENTS

| EP | 1318329 A2 | 6/2003 |
|----|---|---|
| EP | 1619386 B1 | 9/2009 |
| JP | 2001342942 A | 12/2001 |
| WO | WO2013188850 A1 | 12/2013 |

OTHER PUBLICATIONS

European Search Report for related European Application No. 14194515.4, dated May 18, 2015, with English Translation.

* cited by examiner

Fig. 2

| Data descriptor | Standard | Strict | Very strict |
|---|---|---|---|
| Deleting information in non-image attributes, including graphics or superpositions, with respect to: | | | |
| Identity and demographics of the patient | Y | Y | Y |
| Identity of persons involved in the process | Y | Y | Y |
| Identity of the organizations involved in assigning or performing the process | Y | Y | Y |
| Additional information that can be used for treating cases, if access to the originals is guaranteed | Y | Y | Y |
| Private attributes | Y | Y | Y |
| | | | |
| The following profile options are applied: | | | |
| 113101 Delete image data option | - | Y | N/A |
| 113102 Delete detectable visual features option | - | - | - |
| 113103 Delete graphic option | Y | Y | Y |
| 113104 Delete structured-content option | Y | Y | Y |
| 113105 Delete descriptor option | Y | Y | Y |
| 113106 Keep long-term information option – original - | Y | - | - |
| 113107 Keep long-term information option – modified - | - | Y | - |
| 113108 Keep patient characteristic option | Y | - | - |
| 113109 Keep device identity option | Y | Y | - |
| 113110 Keep UID option | Y | - | - |
| 113111 Keep secure private option | Y | Y | - |
| | | | |
| The following proprietary modifications are applied: | | | |
| Remove image data | - | - | Y |

Fig. 3

| Dosage per patient | | |
|---|---|---|
| Dosage for pregnant patients | | |
| Dosage by height | | |
| Dosage by weight | | |
| Dosage by sex | | |
| Dosage by age group | | |
| Dosage by time of day | Dosage by time of day | |
| Dosage by time | Dosage by time | |
| Dosage by CA versus non-CA | Dosage by CA versus non-CA | |
| Dosage per physician | Dosage per physician | |
| Dosage per technician | Dosage per technician | |
| Dosage per body region | Dosage per body region | Dosage per body region |
| Dosage per scanner | Dosage per scanner | Dosage per scanner |
| Dosage per department (unless otherwise busy with an application) | Dosage per department (unless otherwise busy with an application | Dosage per department (unless otherwise busy with an application |
| Dosage per protocol | Dosage per protocol | Dosage per protocol |
| Standard | Strict | Very strict |

Fig. 4

| Age distribution of patients | | |
|---|---|---|
| Average number of scans per patient | | |
| Total number in patient distribution | | |
| Average length of examination | Average length of examination | |
| Number of examinations per hour | Number of examinations per hour | |
| Time between patients | Time between patients | |
| Total number of examination distributions | Total number of examination distributions | |
| Working hours per day (documented) | Working hours per day (documented | |
| Protocol distribution | Protocol distribution | Protocol distribution |
| Body region distribution | Body region distribution | Body region distribution |
| Correlation of body region to protocol | Correlation of body region to protocol | Correlation of body region to protocol |
| Standard | Strict | Very strict |

TRANSMITTING MEDICAL DATA RECORDS

This application claims the benefit of EP 14194515.4, filed on Nov. 24, 2014, which is hereby incorporated by reference in its entirety.

TECHNICAL FIELD

The present embodiments relate to a method for transmitting medical data records from an internal data storage unit to an external data storage unit.

BACKGROUND

Medical facilities, (e.g., hospitals), are increasingly using cloud-based software solutions. These software solutions require sensitive medical patient data to be uploaded into a data center. The upload is performed by a special upload software. The upload software uploads the patient data without anonymization to the data center. The hospital therefore performs an anonymization prior to the actual upload, in order to observe the respective data protection provisions. This procedure is prone to error, time-intensive, and difficult to control. In particular, country-specific data protection provisions apply in different countries. Moreover, it is not possible to provide that the uploaded patient data may be processed in the cloud.

SUMMARY AND DESCRIPTION

The scope of the present invention is defined solely by the appended claims and is not affected to any degree by the statements within this summary. The present embodiments may obviate one or more of the drawbacks or limitations in the related art.

The object of the present embodiments is to automatically adjust patient data records with minimal technical resources such that different data protection guidelines are observed.

According to a first aspect, the object is achieved by a method for transmitting medical data records, having the acts of receiving a patient data record from an internal data storage unit; selecting an anonymization setting from a set of predetermined anonymization settings; generating an anonymized patient data record on the basis of the selected anonymization setting; and transmitting the anonymized patient data record to an external data storage unit. As a result, the technical advantage is achieved for instance in that a set of anonymization settings is used, which may be adjusted to different functions of the external data storage unit. To this end, a set of properties of frequently used services of the external data storage unit may be used, which are defined for each anonymization setting. Moreover, there is the option of selecting an anonymization setting during the use of software in a medical facility as a function of the place of installation of the external data storage unit.

In an advantageous embodiment of the method, the anonymized patient data record is stored in the external data storage unit. As a result, the technical advantage is achieved for instance that the patient data record is permanently available.

In a further advantageous embodiment of the method, the anonymization setting is automatically selected on the basis of a location of the external data storage unit. As a result, the technical advantage is achieved for instance that permissible patient data records are present at the location of the external data storage unit.

In a further advantageous embodiment of the method, the anonymized patient data record includes a logical link to the selected anonymization setting. As a result, the technical advantage is achieved for instance such that the anonymization setting may be determined on the basis of the anonymized patient data record.

In a further advantageous embodiment of the method, the received and/or the anonymized patient data record is a DICOM file. As a result, the technical advantage is achieved for instance in that a particularly suitable format is used to store and process the patient data records.

In a further advantageous embodiment of the method, the anonymization setting is embedded in the anonymized patient data record. As a result the technical advantage is achieved for instance such that the anonymization setting is contained in the anonymized patient data record.

In a further advantageous embodiment of the method, the anonymized patient data record is stored in the internal data storage unit. As a result, the technical advantage is achieved for instance such that the anonymized patient data record is additionally stored.

In a further advantageous embodiment of the method, the data of the patient data record, which is anonymized when the anonymized patient data record is generated, is stored in an additional non-anonymized data record. As a result the technical advantage is achieved for instance such that the data is also available despite anonymization.

In a further advantageous embodiment of the method, a mapping is generated between the non-anonymized data record and the anonymized patient data record. As a result, the technical advantage is achieved for instance such that the data may be assigned to an anonymized patient data record.

In a further advantageous embodiment of the method, the mapping is stored encrypted. As a result, the technical advantage is achieved for instance such that non-authorized access to the mapping data is prevented.

In a further advantageous embodiment of the method, the external data storage unit transfers a service parameter indicating which services are provided by the external data storage unit. As a result, the technical advantage is achieved for instance such that the method may use this parameter for further decision-making processes.

In a further advantageous embodiment of the method, the anonymization setting is selected on the basis of the service parameter. As a result, the technical advantage is achieved for instance such that patient data records that may be processed by the services are generated depending on the current service.

In a further advantageous embodiment of the method, the anonymization setting may be deactivated. As a result, the technical advantage is achieved for instance such that the patient data records may if necessary be transmitted unchanged.

In a further advantageous embodiment of the method, the anonymized patient data record is encrypted prior to transmission. As a result, the technical advantage is achieved for instance such that data security is increased again.

According to a second aspect, the object is achieved by a computer system for transmitting medical data records, having a receiving facility for receiving a patient data record from an internal data storage unit; a selection facility for selecting an anonymization setting from a predetermined set of anonymization settings; a generation facility for generating an anonymized patient data record on the basis of the selected anonymization setting or rule; and a transmit facility for transmitting the anonymized patient data record and the encrypted patient identification data record to an external data storage unit. As a result, the same technical advantages are achieved as by the method according to the first aspect.

BRIEF DESCRIPTION OF THE DRAWINGS

Exemplary embodiments are depicted in the drawings and are described in more detail below.

FIG. 2 depicts an example of a table with DICOM data.
FIG. 3 depicts exemplary properties of a dose management service.
FIG. 4 depicts exemplary properties of a scanner-utilization service.

DETAILED DESCRIPTION

Figure 1:
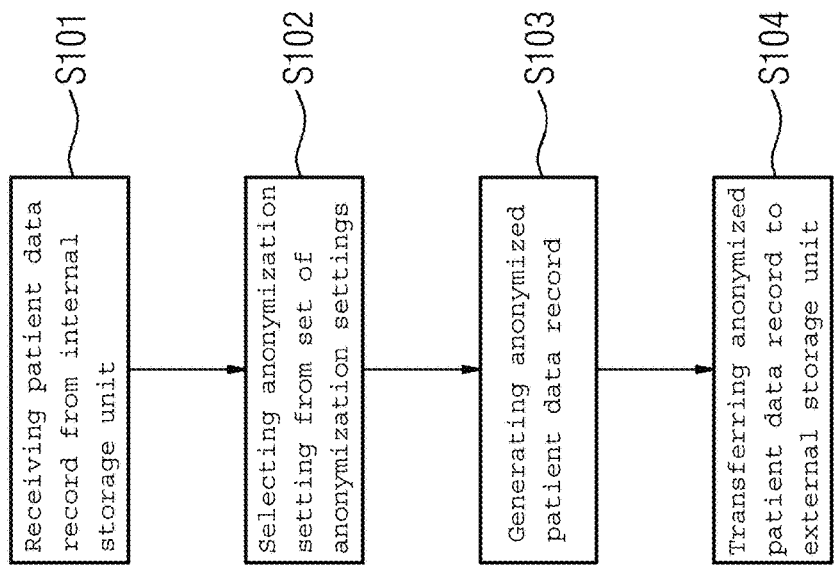
FIG. 1 depicts a block diagram of an exemplary method.

FIG. 1 depicts a block diagram of the method for transferring medical data records. In act S101, a patient data record is received from an internal data storage unit. The internal data storage unit may be formed by a picture archiving and communication system (PACS) within a hospital.

An anonymization setting is selected in act S102 from a set of predetermined anonymization settings. The selection may be performed automatically as a function of a location of the external data storage unit or the processing functions of the external data storage unit. An anonymized patient data record is generated in act S103 on the basis of the selected anonymization setting. Certain data of the patient data record is anonymized in the process, for instance by patient identification data being removed or being replaced by random data. The anonymized patient data record is transferred in act S104 to an external data storage unit. By way of example, the external data storage unit is formed by a cloud in the internet.

The method is used for automated data protection management on a server, which uploads medical patient data records from a hospital into a cloud data center as an external data storage unit. The method may be executed on a server by an upload software, which is used globally in any hospital and which automatically supports and applies locally applicable data protection provisions as a function of the country of operation and the cloud services used.

Moreover, it is possible to provide technically that the anonymization or pseudonymization of the patient data is performed by the upload software such that the cloud services may process the uploaded patient data. As a result, a situation may be prevented in which the anonymized or pseudonymized patient data may not be used by the cloud services.

The set of predetermined anonymization settings may include for instance three anonymization settings, which may be used in a majority of data protection cases. A distinction may be made here between a standard anonymization setting, a stringent anonymization setting, and a very stringent anonymization setting.

FIG. 2 depicts a table of DICOM data, which is uploaded by the medical facility into the cloud as a function of the anonymization setting. A distinction is made here between three predetermined anonymization settings, (e.g., a standard anonymization setting, a stringent anonymization setting, and a very stringent anonymization setting). Depending on the anonymization setting selected, the patient data record is processed differently. For instance, image data is removed from the patient data records under the very stringent anonymization setting, while this is not the case with the standard anonymization setting and the stringent anonymization setting.

The cloud may provide different services for processing the patient data records. For instance, it is possible to provide a dose management service, a scanner utilization service, or an image sharing service.

FIG. 3 depicts the properties of a dose management service as a function of the anonymization setting. The dose per patient is evaluated for instance in a standard anonymization setting, whereas this is not performed with a stringent or very stringent anonymization setting.

FIG. 4 depicts the properties of a scanner utilization service as a function of the anonymization setting. With a standard anonymization setting, the patient age distribution is evaluated for instance, whereas this is not performed with a stringent or very stringent anonymization setting.

The image sharing service is only comprehensively available in the standard anonymization setting. This is not available in the case of a stringent anonymization setting. The reason for this is that the image sharing service requires an upload of patient data from a hospital into the cloud and this is only possible with the standard anonymization setting.

Different patient data records that may be uploaded by the hospital into the cloud by the upload software exist as a function of the anonymization setting. For this purpose, the cloud may also transfer a service parameter, which indicates which services are provided in the cloud. Moreover, a location of the cloud may also be transferred, for instance in the form of geographical coordinates or a country code. The service parameter or the location are evaluated by the method. An anonymization setting is automatically selected on the basis of this evaluation, the anonymization setting generating the patient data records including the required patient data.

Figure 5:
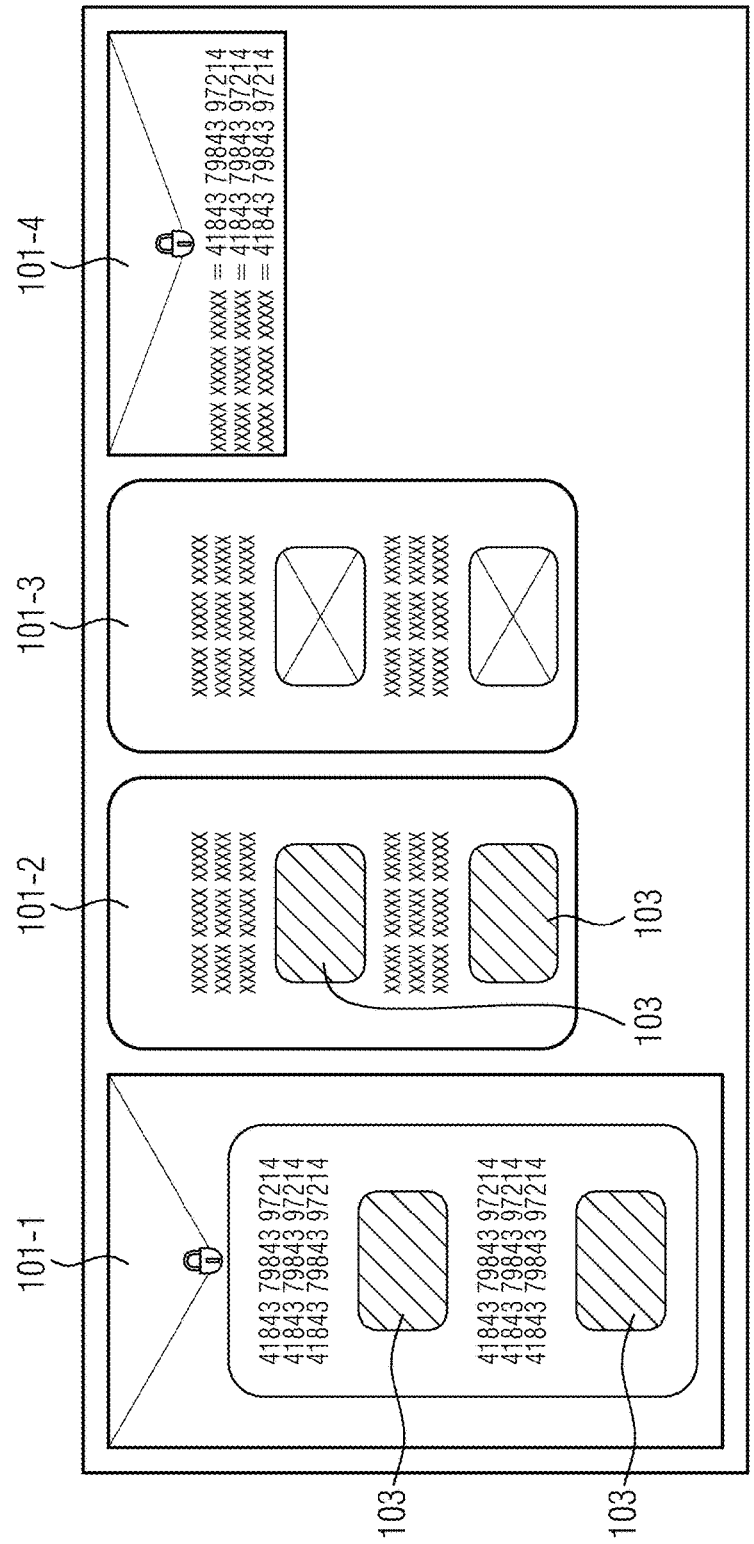
FIG. 5 depicts a schematic view of an example of different patient data records.

FIG. 5 depicts a schematic view of different patient data records 101-1, . . . 101-4. The patient data record 101-1 is an original DICOM file, which is encrypted. The patient data record 101-1 has the image files 103.

The patient data record 101-2 is a DICOM file with original image data and header date, which have been anonymized by a first predetermined anonymization setting. The patient data record 101-2 likewise includes the image data 103.

The patient data record 101-3 is a DICOM file without image data and with header data, which have been anonymized by a second predetermined anonymization setting. The patient data record 101-4 is an encrypted file, which includes an mapping between the anonymized header data and the original header data.

Figure 6:
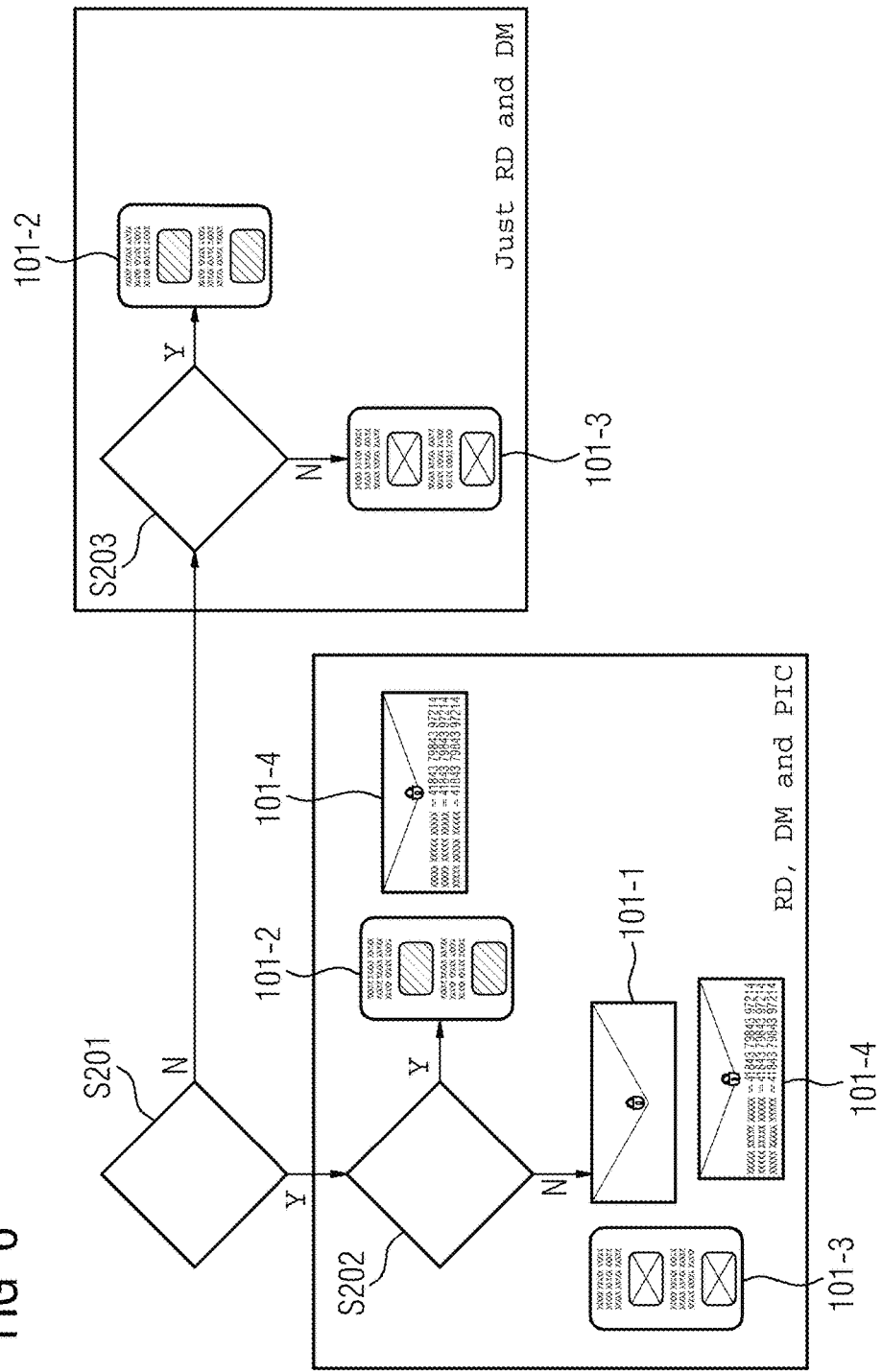
FIG. 6 depicts an example of a display of the logic.

FIG. 6 depicts a display of the logic, which is implemented in an upload software and which is applied to the upload of the patient data records 101-1, . . . 101-4 as a function of the anonymization setting.

It is determined in act S201 whether an image sharing service is provided by the cloud. If this is the case, it is determined in act S102 whether an image data record is provided. If the image data record is provided, the patient data records 101-2 and 101-4 are transferred. If the image data service is not provided, the patient data record 101-3 is transferred together with the original patient data record 101-1 and the patient data record 101-4. A processing of the patient data records 101-1, . . . , 101-4 may take place by the image sharing service, the dose management service or the scanner utilization service. If the image sharing service is activated, this points to the standard anonymization setting.

If it is determined in act S201 that no image sharing service is provided by the cloud, it is determined in act S103 whether an image data service is provided. If the image data service is provided, the patient data record 101-2 is transferred. If this is not the case, the patient data record 101-3 is transferred. A processing of the patient data records 101-1 and 101-3 takes place in this case by the dose management service or the scanner utilization service. Examples of user interfaces of cloud services are explained below.

Figure 7:
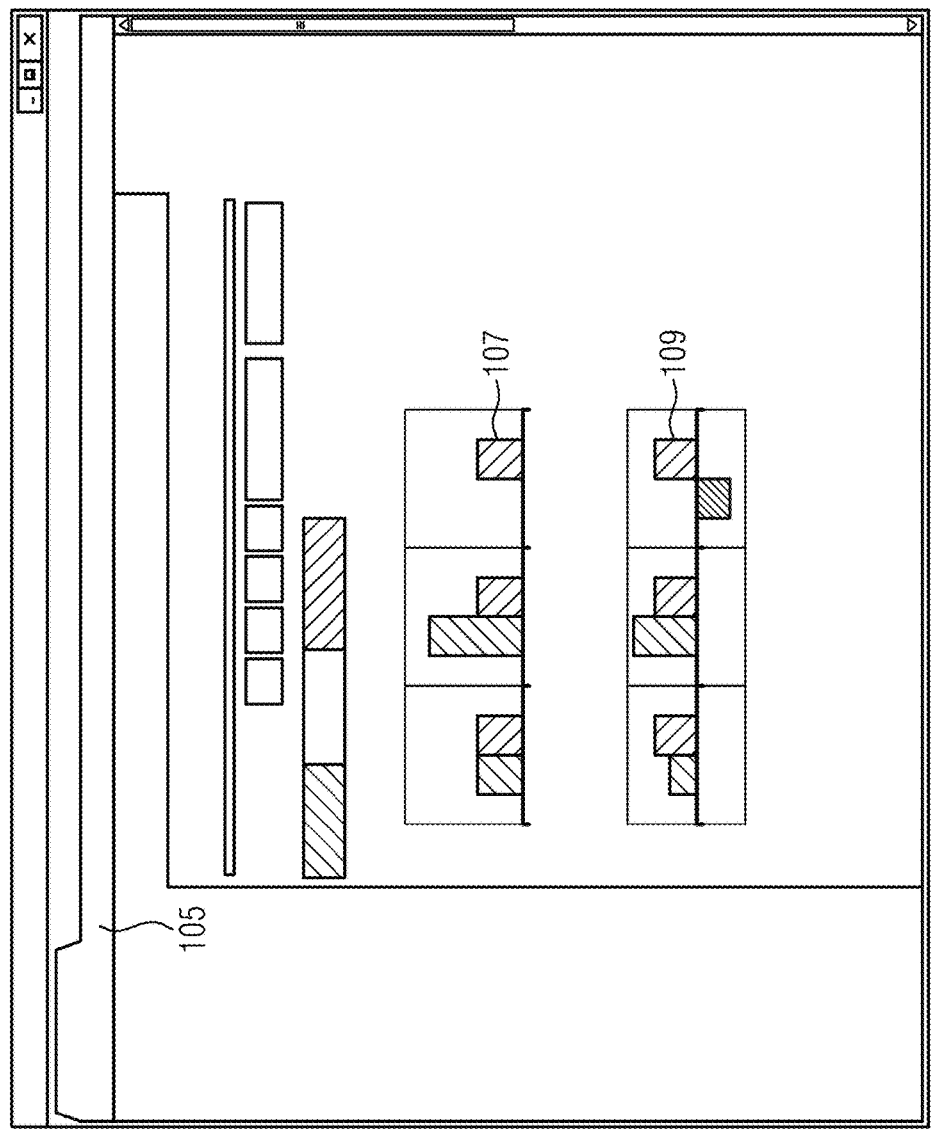
FIG. 7 depicts an example of a user interface.

FIG. 7 depicts an example of a user interface 105 of a scanner utilization in the case of a stringent anonymization setting. In this user interface 105, the duration of an examination and the examinations per hour for certain devices are indicated in field 107 and field 109, respectively.

Figure 8:
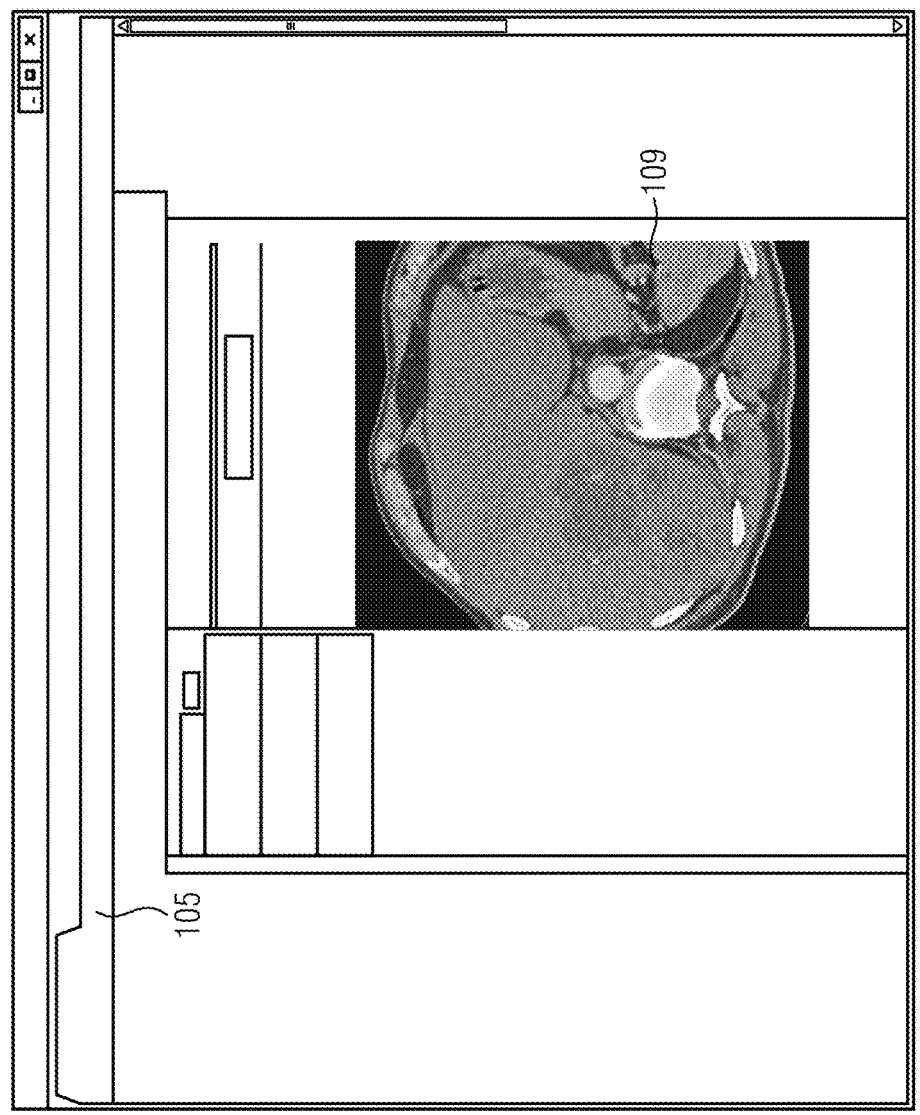
FIG. 8 depicts a further example of a user interface.

FIG. 8 depicts an example of a user interface 105 of an image sharing service in the case of a standard anonymization setting. Image data is indicated in field 109.

Figure 9:
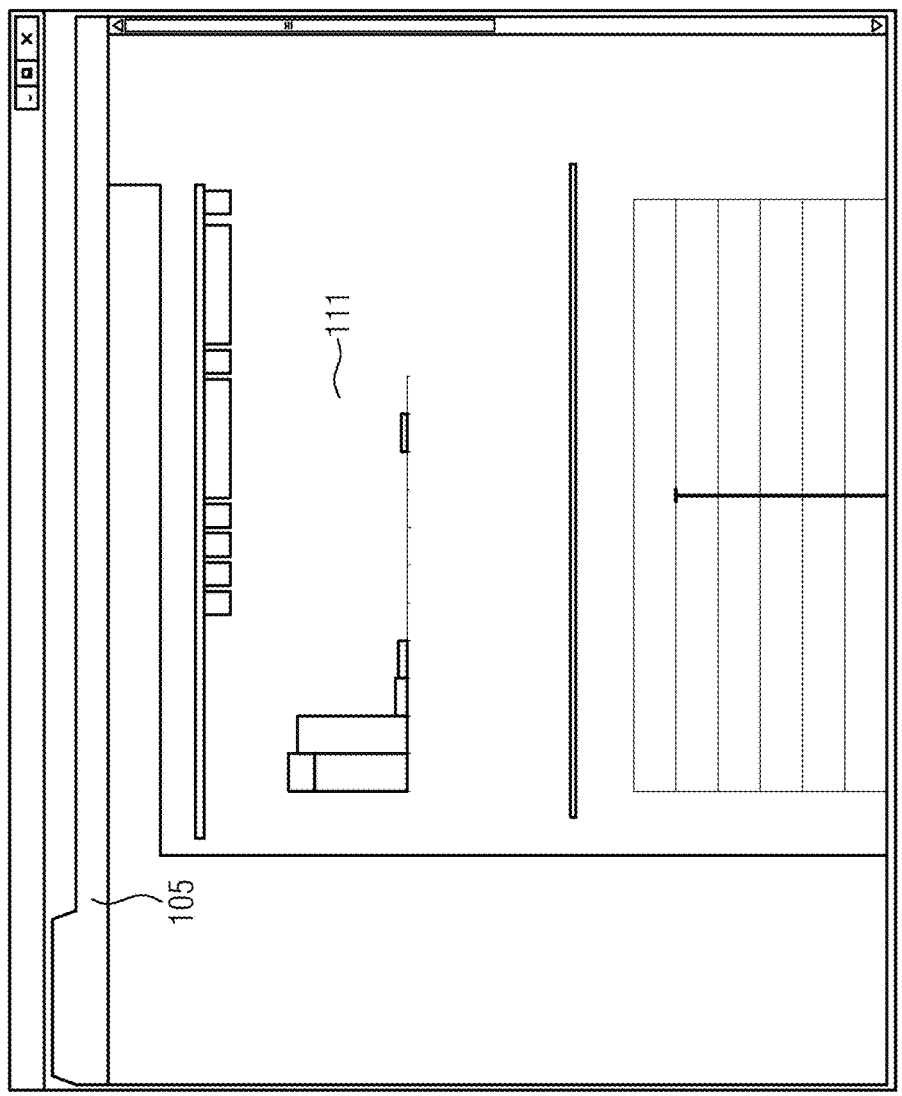
FIG. 9 depicts a further example of a user interface.

FIG. 9 depicts an example of a user interface 105 of a dose management service with a very stringent anonymization setting. The temporal course of a dose is indicated in field 111.

Figure 10:
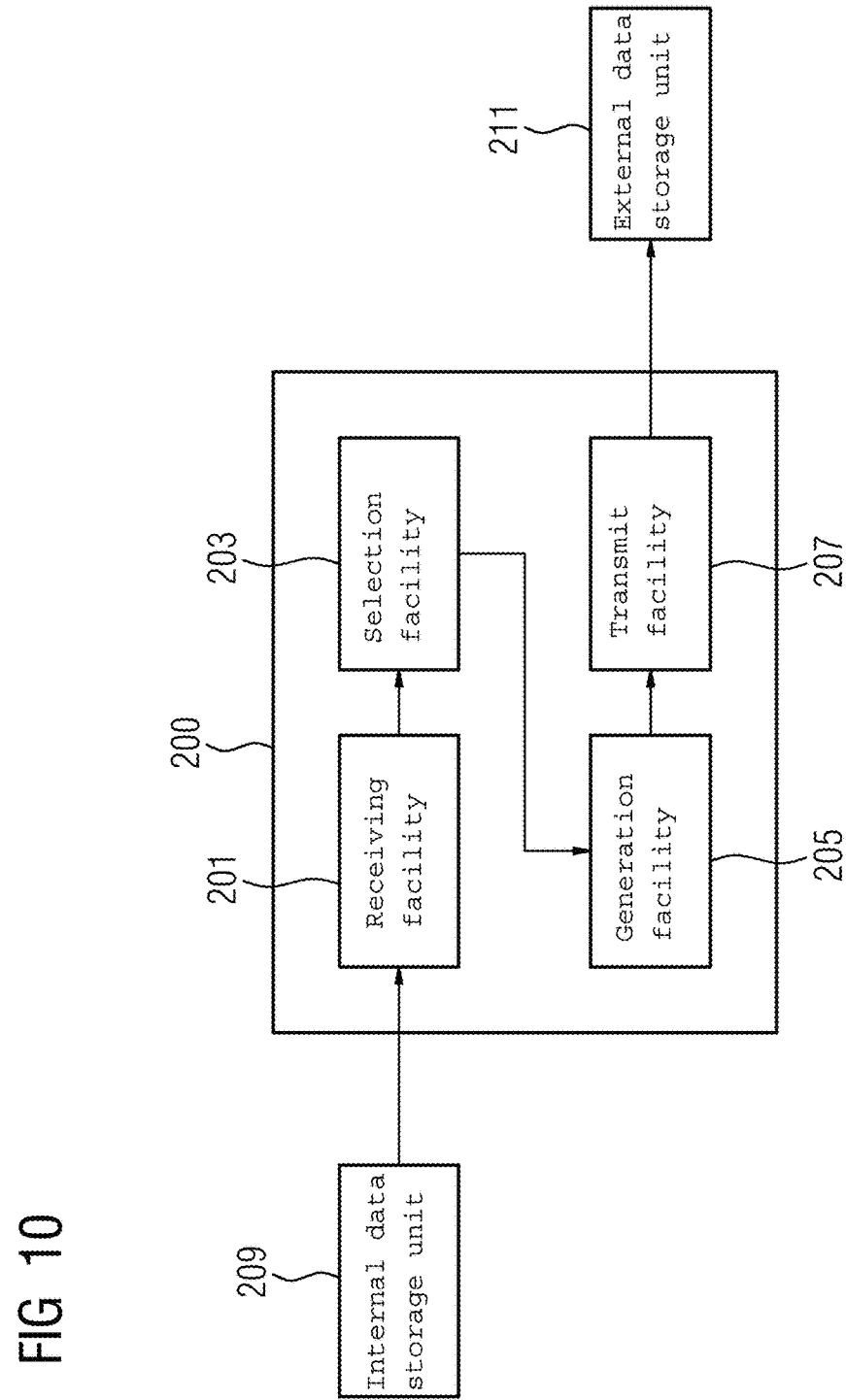
FIG. 10 depicts an example of a computer system for transmitting medical data records.

FIG. 10 depicts a computer system 200 for transmitting medical data records. The computer system 200 includes a receiving facility 201 for receiving a patient data record from an internal data storage unit 209. A selection facility 203 of the computer system 200 serves to select an anonymization setting from a predetermined set of anonymization settings. A generation facility 205 serves to generate the anonymized patient data record 101-2, 101-3 on the basis of the selected anonymization setting or rule. The transmit facility 207 serves to transmit the anonymized patient data record 101-2, 101-3 to an external data storage unit 211. The receiving facility 201, the selection facility 203, the generation facility 205, and the transmit facility 207 may be implemented by software or hardware.

The method uses a set of anonymization settings, which may be adjusted globally to different countries. Moreover, a set of properties of frequently used cloud services is used, which are defined for each anonymization setting. As a result, there is the option of selecting an anonymization setting during the use of software in a medical facility as a function of the place of installation. Moreover, there is the option of processing the data in all cloud services regardless of the anonymization setting used. A consistency between the anonymization settings and the ability of the cloud services to process the uploaded data is provided by the technical design. Moreover, there is the option of resetting the anonymization settings. A resetting of the anonymization settings may prove to be useful if a medical facility increases or reduces the number of services that are used in the cloud.

If a hospital decides for instance to use an image sharing service in the cloud, this applies new anonymization settings compared with those that were previously used, since the image sharing service requires an uploading of image data into the cloud. The selection and assumption of new anonymization settings or rules may be performed by a mouse click, since further adjustments to the patient data record are automatically performed.

The uploading of patient data records is performed automatically and the properties of a dose management service, service utilization service and image sharing service are automatically adjusted to the setting.

The method is in conflict with existing approaches, in which the hospital may not automatically change the patient data records on the basis of an anonymization setting. In this case the operation of processing services provided may not be provided.

All features depicted and explained in conjunction with the individual embodiments of the invention may be provided in a different combination in the inventive subject matter in order at the same time to realize its advantageous effects.

The scope of protection of the present invention is provided by the claims and is not restricted by the features explained in the description or depicted in the Figures.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for transmitting medical data records, the method comprising:
   receiving a patient data record from an internal data storage unit;
   automatically selecting an anonymization setting from a set of predetermined anonymization settings based on a geographic location of an external data storage unit, wherein the set of predetermined anonymization settings comprises varying levels of stringency, and wherein a first level of stringency is automatically selected based on a physical location of the external data storage unit being in a first geographic location, and a second level of stringency is automatically selected based on the physical location of the external data storage unit being in a second geographic location;
   generating an anonymized patient data record based on the selected anonymization setting; and
   transmitting the anonymized patient data record to the external data storage unit.

2. The method as claimed in claim 1, wherein the anonymized patient data record is stored in the external data storage unit.

3. The method as claimed in claim 1, wherein the anonymized patient data record comprises a logical link to the selected anonymization setting.

4. The method as claimed in claim 1, wherein the received patient data record, the anonymized patient data record, or each of the received patient data record and the anonymized patient data record is a digital imaging and communications in medicine (DICOM) file.

5. The method as claimed in claim 1, further comprising:
embedding the anonymization setting in the anonymized patient data record.

6. The method as claimed in claim 5, further comprising: storing the patient data record in an additional non-anonymized patient data record.

7. The method as claimed in claim 6, further comprising: generating a mapping between the non-anonymized patient data record and the anonymized patient data record.

8. The method as claimed in claim 5, further comprising: storing the anonymized patient data record in the internal data storage unit.

9. The method as claimed in claim 8, further comprising: encrypting the anonymized patient data record prior to transmission.

10. The method as claimed in claim 1, further comprising: storing the anonymized patient data record in the internal data storage unit.

11. The method as claimed in claim 1, further comprising: storing the patient data record, which is anonymized when the anonymized patient data record is generated, in an additional non-anonymized patient data record.

12. The method as claimed in claim 11, further comprising:
generating a mapping between the non-anonymized patient data record and the anonymized patient data record.

13. The method as claimed in claim 12, wherein the mapping is stored encrypted.

14. The method as claimed in claim 1, further comprising: transferring, by the external data storage unit, a service parameter indicating which services are provided by the external data storage unit.

15. The method as claimed in claim 14, wherein the anonymization setting is selected based on the service parameter.

16. The method as claimed in claim 1, further comprising: encrypting the anonymized patient data record prior to transmission.

17. The method as claimed in claim 1, wherein the varying levels of stringency comprise at least three levels of stringency.

18. The method as claimed in claim 1, wherein the first level of stringency removes patient identity data but not image data from the patient data record, and the second level of stringency removes both the patient identity data and the image data from the patient data record.

19. The method as claimed in claim 1, wherein the first geographic location is a first country, and the second geographic location is a second country.

20. A device for transmitting medical data records, the device comprising:
an internal data storage unit;
a receiving facility for receiving a patient data record from the internal data storage unit;
a selection facility for automatically selecting an anonymization setting from a predetermined set of anonymization settings based on a geographic location of an external data storage unit, wherein the set of predetermined anonymization settings comprises varying levels of stringency, and wherein a first level of stringency is automatically selected based on a physical location of the external data storage unit being in a first geographic location, and a second level of stringency is automatically selected based on the physical location of the external data storage unit being in a second geographic location;
a generation facility for generating an anonymized patient data record based on the selected anonymization setting; and
a transmit facility for transmitting the anonymized patient data record to the external data storage unit.

* * * * *